(12) United States Patent
Lee et al.

(10) Patent No.: US 6,485,427 B1
(45) Date of Patent: Nov. 26, 2002

(54) COMPRESSIBILITY PROBE FOR MONITORING BLOOD VOLUME CHANGES

(76) Inventors: Jen-Shih Lee, 3375 Blandemar Dr., Charlottesville, VA (US) 22903; Lian-Pin Lee, 3375 Blandemar Dr., Charlottesville, VA (US) 22903

( * ) Notice: Subject to any disclaimer, the term of this patent is extended or adjusted under 35 U.S.C. 154(b) by 0 days.

(21) Appl. No.: 09/908,223

(22) Filed: Jul. 18, 2001

Related U.S. Application Data
(60) Provisional application No. 60/218,906, filed on Jul. 18, 2000.

(51) Int. Cl.$^7$ .................................................. A61B 8/00
(52) U.S. Cl. ....................................... 600/468; 600/437
(58) Field of Search ................................. 600/458, 443, 600/447, 437, 485, 500, 475, 300; 128/903

(56) References Cited

U.S. PATENT DOCUMENTS

| | | | |
|---|---|---|---|
| 5,964,701 A | * | 10/1999 | Asada et al. ............... 128/903 |
| 6,080,107 A | * | 6/2000 | Poland ....................... 600/458 |
| 6,280,390 B1 | * | 8/2001 | Akselrod et al. ........... 600/475 |

* cited by examiner

Primary Examiner—Francis J. Jaworski
Assistant Examiner—Maulin Patel
(74) Attorney, Agent, or Firm—Sheldon H. Parker (57) ABSTRACT

An apparatus and method to assess the compressibility of blood includes a combination of ultrasound transducers attached to tubing in which blood is flowing. An indicator medium is injected into the bloodstream of the subject over one or more time points and ultrasound waves are transmitted and monitored using transducers and phase lock amplifier to assess transmission time. Using a linear relationship between compressibility and density, changes in blood density are calculated from changes in transmission time to predict blood density changes and then the blood volume and microvascular pooling. This information allows prediction of complications that can occur during hemodialysis or because of post-traumatic fluid replacement and development of therapy to alleviate the complications.

21 Claims, 5 Drawing Sheets

COMPRESSIBILITY PROBE FOR MONITORING BLOOD VOLUME CHANGES

RELATED U.S. APPLICATIONS

This application claims priority to U.S. Provisional Application 60/218,906, filed Jul. 18, 2000.

FIELD OF THE INVENTION

This invention relates to systems and methods for non-invasive, continuous monitoring of a patient's blood density changes in order to determine the blood volume and microvascular pooling of the patient over time.

BACKGROUND

An apparatus and method are described to monitor the time of sound transmission in the blood stream of a patient and use a linear relationship between compressibility and density for accurate and sensitive assessment of blood density changes due to saline or dialysate dilution. With an appropriate protocol, the density changes are used to determine the blood volume and microvascular pooling of the patient over time.

Hypotension and hypovolemia are common circulatory problems that occur during shock (Chien et al, *American Journal of Physiology*, 210:1411–1418), traumatic injury, dialysis (Amerling et al in *Clinical Dialysis* $3^{rd}$ Edition, Appleton and Lang editors, 1995) and surgical interventions. A variety of disorders and injuries are related to the occurrence of hypotension (Daugirdas, *Kidney International* 39:233–246). Fluid losses related to burn injury or hemorrhage due to trauma are examples of situations where compensation for such loss is necessary. Compensation is typically done by infusing isotonic saline, plasma or other physiological solutions into the circulation until arterial pressure is elevated to normal. Although blood volume reduction correlates with reduction in arterial pressure under laboratory simulations of injury and anesthesia, actual occurrences of traumatic blood loss often show only slightly reduced arterial pressures due to the body's neural compensation mechanisms. Once these mechanisms reach their limits, arterial pressure can drop rapidly. The management of this subnormal arterial pressure is critical to survival; immediate restoration of arterial pressure after traumatic injury can cause more problems than allowing the pressure to remain subnormal. Rapid restoration of arterial pressure results in higher oxygen demand and can dislodge clots that have started to provide homeostasis.

While the body's compensation mechanisms are important to survival, limitations exist in the ability to determine several factors including the volume of blood loss, the distribution of blood volume between the microcirculation and macrocirculation, the necessary volume for infusion, and whether overexpansion of the blood volume has occurred after infusion. Arterial pressure monitoring is unable to provide sufficient information to address these concerns. A need exists for precise monitoring of changes to blood volume and microvascular pooling in patients, particularly over extended time periods.

Beyond traumatic injury, a number of medical procedures require such precise monitoring of blood volume. Invasive surgery and dialysis are two common situations where monitoring blood volume changes provide important information related to the outcome of the procedure. For example, 15% to 40% of patients undergoing dialysis in the United States will experience hypotension and, occasionally, circulatory shock. Milder symptoms include muscle cramping and lightheadedness. These dialysis related side effects are implicated in reduced dialysis efficacy.

Dialysis and systems for dialysis are well known in the art. These work by extracting a significant fraction of fluid from the circulating blood. Compensation for this reduction in blood volume normally occurs through fluid restituted from the tissue. The activation of the microcirculation by hemodialysis leads to pooling of blood in the microcirculation affecting a low venous return, poor cardiac filling, lowered cardiac output and then hypotension. For patients undergoing a well-controlled fluid removal, these cardiovascular changes, and not hypovolemia, are the reason for hypotension development during the course of hemodialysis. Using saline or dialysate dilution, we can monitor the change in blood volume over regular times, for example every half hour. A continuous change in blood density can be analyzed and microvascular pooling within the circulation can be determined. These parameters can be used by physicians to carefully monitor the cardiovascular changes that are responsible for the development of hypotension in dialysis patients.

The use of velocity measurements in blood to assess blood volume has been attempted and described previously. Krivitski, in U.S. Pat. Nos. 5,453,576 and 5,685,989 describes an apparatus and method for measuring several hemodynamic parameters by using a sound velocity sensor. The information contained in the '576 and the '989 patent is incorporated by reference as though cited in its entirety. The technique described uses a linear approximation of a non-linear relationship between the sound velocity and the density of the blood. This approximation introduces additional error into the volume computation, which limits the sensitivity and accuracy of the system. Further, the '576 patent is limited to large variations in sound velocity which make it inaccurate to assess blood volume.

The system patented by Schneditz in U.S. Pat. No. 5,830,365 also utilizes sound velocity for the measurement of total protein concentration, and then the blood volume by altering the dialyzer to run at a different ultrafiltrate extraction rate. These two methods are limited to large variations in sound velocity and the requirement of no blood pooling to the microcirculation.

Several other devices exist which are used to monitor blood volume or blood parameter changes. These include the Know-Recirc™ hematocrit measurement device produced by H.& H. Control Systems (Jackson, Miss.) and described in U.S. Pat. No. 5,312,550 and an optical device marketed under the Crit-Line® platform and the Transcutaneous Access Flow device by HemaMetrics Corporation (Boston, Mass.) described in U.S. Pat. No. 5,499,627 and 6,117,099. These devices continuously monitor the change in hematocrit over a dialysis session. Increases in hematocrit over the session are interpreted as a decrease in plasma volume thereby theoretically providing a mechanism for monitoring blood volume changes. This method does not account for the Fahraeus effect where microvascular pooling of blood can result in an increase in hematocrit. By not correcting for microvascular pooling, blood volume changes estimated by this device are off by a factor of two or more. Again, sensitivity of this device is limited and can cause incorrect diagnoses or treatments. A similar problem exists in the work of Polaschegg in U.S. Pat. No. 5,230,341. Correction for microvascular pooling and sensitivity are deficient in the '341 patent and incorrect results on the projected blood volume occur leading to potentially harmful treatments.

SUMMARY OF THE INVENTION

The present invention provides a method and compressibility probe to accurately and reliably determine compressibility and density of blood due to the infusion of saline or dialysate for the quantification of blood volume or microvascular pooling in patients. The invention utilizes blood density changes over time while accounting for the effect of the microcirculation to provide medical professionals with valuable information on microvascular pooling for the prevention of complications related to trauma and hemodialysis.

Further, the present invention measures the phase shift between emitting ultrasound and receiving ultrasound, converts the phase shift to transmssion time and subsequently to sound velocity in a corporeal or extracorporeal system, and uses the linear relationship between blood compressibility and density to calculate from sound velocity blood compressibility and blood density.

The novel embodiments of the compressibility probe provide significant advantages over the prior art. These include: (1) a better method to determine sound velocity because of the use of higher ultrasound frequency and the procedure for phase shift detection; (2) a better method to determine the density and compressibility of blood by using a precise linear relationship between them instead of an approximation; (3) a new procedure which includes the infusion of isotonic saline and shifting of blood between the circulation and an extracorporeal system; (4) a better interpretation of density changes through either a change in blood volume or through a redistribution of blood volume between the microcirculation and the macrocirculation; and (5) better quantification of microvascular pooling. The combination of these five features enables the compressibility probe to achieve high resolution and to provide crucial information for the physician to select an effective strategy to prevent or treat hypotension in any patient.

Blood is a mixture of cells and plasma. The density and compressibility of blood is the sum of its components weighted by the volume fraction. The velocity of ultrasound in blood is related to a variety of factors, including its hematocrit, plasma protein concentration, and total protein concentration. Likewise, blood compressibility also relates to hematocrit, plasma protein concentration, and total protein concentration. These relationships are difficult to identify because of a lack of accurate measurement systems. Attempts at relating variable factors have deduced approximations to be utilized by the system described in the '576 patent and in the Know-Recirc™ and the Crit-Line® hematocrit measurement system. These empirical approximations limit the accuracy and sensitivity of the measurement system and introduce error into the analysis.

The more accurate calculation of blood volume and its distribution s taught herein are used to monitor and treat patients more effectively. Software and hardware are configured to generate and receive the ultrasound wave and use the information to monitor the changes to blood volume and redistribution of blood volume in patients. Methods for interfacing the data generated by the compressibility monitoring technique with analytical machinery and additional uses for the compressibility monitoring will become apparent to those of skill in the art based on the description contained herein.

DESCRIPTION OF THE PREFERRED EMBODIMENTS

The instant invention incorporates a novel linear relationship between compressibility and density to interpret ultrasound velocity measurement. This relationship is not explicitly influenced by hematocrit, plasma protein concentration, blood density or plasma density. The linear relation is supported by the fact that blood is a mixture. As a result, the method improves accuracy of the overall assessment. Processing of ultrasound transducer signals at high frequency is used to assess density and compressibility of the blood. A continuous wave of ultrasound is emitted by an ultrasound transducer excited at an appropriate frequency (f in the range of 10 to 30 MHz). The ultrasound passes through the bloodstream and the tubing. The transmitted ultrasound wave as picked up by the receiving transducer is compared with the emitting wave to determine Time Shift ($T_{shift}$), which is the time of the receiving wave shifted from the emitting wave. The value of Time Shift reported is normally within $\pm 0.5\ T_0$. The period of ultrasound $T_0$ is also $1/f$. The actual delay in the transmission of this continuous ultrasound contains an integer multiple of the period, $n(T_0)$. The overall transmission time is equal to $[T_{shift}+n(T_0)]$ and is composed of two delays: the transmission time through the fluid domain such as flowing blood or saline, and the transmission time through the tube walls and the delay on the signal transmission through the cables connecting the transducers to the phase shift device and functional generator. Where $T_2$ is defined to include the tube wall transmission time and the cable delay, L is the distance between the inner walls of the tube and c is the ultrasound velocity of blood, a relationship between these parameters is described in Equation 1.

$$c=L/[T_{shift}+(nT_0)-T_2] \qquad \text{Equation 1}$$

When the tube is filled with water or saline (fluids with known ultrasound velocities), a measurement for $T_{shift}$ provides two measurements to solve for L and $[(nT_0)-T_2]$, thus the ultrasound velocity in blood coming out of any dialysis or vascular technique can be determined by this data processing procedure.

The ultrasound velocity and the density in blood ($\rho$) are related to compressibility ($\kappa$) as shown in Equation 2.

$$\kappa=\rho/c^2 \qquad \text{Equation 2}$$

Tests with ultrasound and the transducer system described herein demonstrate that the compressibility calculated using this relationship is linearly related to the density by a slope (b) and an x-intercept (a) as in Equation 3.

$$\kappa=a+b\rho \qquad \text{Equation 3}$$

This relationship holds over a wide range of hematocrit, plasma protein concentrations, blood densities and plasma densities. Equation 2 and Equation 3 are combined to accurately solve compressibility and density from the measurement of velocity, allowing a more accurate determination by the density dilution method for determining blood volume than previously described.

Density dilution methods are well known methods for blood volume determination. A bolus of isotonic saline at approximately two to three per cent of the total blood volume is infused into the circulation. The saline density is lower than the blood density and mixing of the saline with the circulating blood leads to a reduction in blood density. Where $\rho_1$ and $\rho_2$ are the density of the blood prior to and after the infusion of isotonic saline, $\rho_3$ is the density of saline and $\Delta V$ is the increase in total blood volume due to the bolus of saline a novel relationship exists between these densities and the total blood volume ($V_b$) of the patient. This relationship is shown in Equation 4.

$$V_b = A[\Delta V(\rho_2 - \rho_3)/(\rho_1 - \rho_2)] \qquad \text{Equation 4}$$

The constant A varies slightly by species and accounts for the Faehraeus effect in the microcirculation. The constant A is approximately equal to 1.14 for human and rabbit and can be determined for any animal. The dilution can be repeated over time, for example every hour, to assess the temporal change in blood volume.

Over one hour of hemodialysis treatment, one blood volume measurement is carried out at the beginning and another at the end. These two measurements determine the change in blood volume ($\Delta V_b$). In the time between these two measurements, the compressibility probe monitors the blood density and the dialysis machine will report the ultrafiltrate removed from the patient as $\Delta V_{dialysis}$. If the blood density right after the first blood volume measurement is defined as $\rho_4$ and the blood density before the second blood volume measurement is defined as $\rho_5$, the corresponding hematocrits are $H_4$ and $H_5$. Then the pooling of the blood to the microcirculation can be calculated from Equation 5.

$$\Delta V_{pooling} = G\{V_b(\rho_4-\rho_5)F_{cell}/(\rho_4-\rho_p)+(\Delta V_{dialysis}-2\Delta V_b)[(1-H_4)/(1-F_{cell}H_4)](\rho_p-\rho_3)/[3(\rho_4-\rho_p)]-\Delta V_b\} \qquad \text{Equation 5}$$

Where $\rho_p$ is the density of plasma right after the first blood volume measurement and $\rho_3$ is the density of the ultrafiltrate or saline, the constant $F_{cell}$ is 0.87, the constant G is 2.78. The amount of pooling is indicative of how the patient is susceptible to microvascular pooling.

Figure 1A:
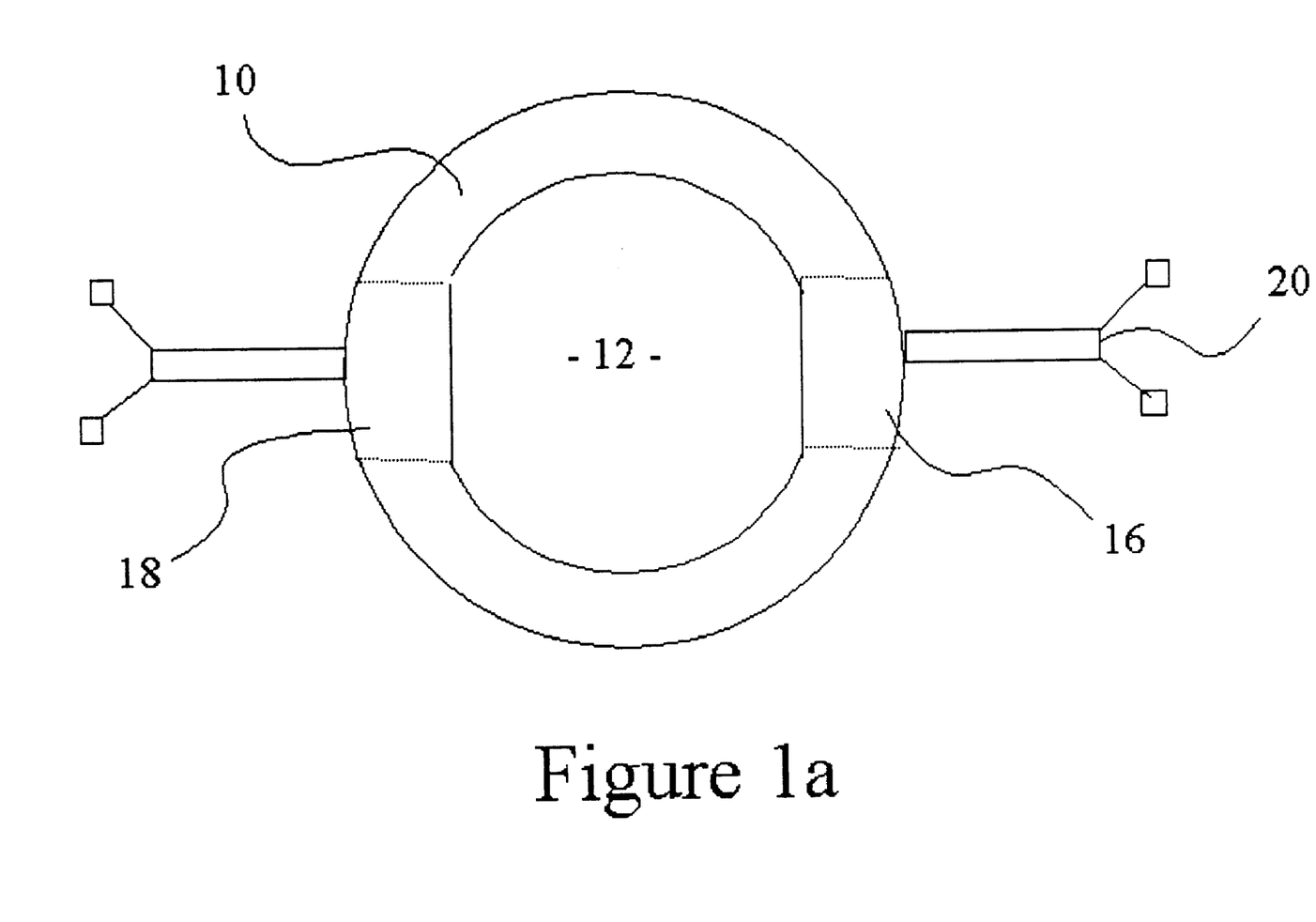
FIG. 1a is a schematic drawing of a first embodiment of the compressibility probe.

Several working models of the cardiac compressibility probe have been developed. FIG. 1a depicts one embodiment of the compressibility probe with the ultrasound transducers in direct contact with the blood. A thick walled tube 10 has a pair of ultrasound transducers 16, 18 mounted onto the two opposite walls. Fluid, such as blood or plasma, flows along the interior 12 of the tube 10. In the original signal processing, the transducer 16 is activated by any commercially available pulser/receiver, including a Panametrics 5072PR pulser/receiver, to emit ultrasound impulses of about 15 to 20 Megahertz at a rate of about 100 Hertz. After its transmission through the flowing blood, the second transducer 18 receives the ultrasound signal. The trigger signal from the pulser/receiver triggers a digital oscilloscope such as a LeCroy 9350AL oscilloscope or a Synatec Analog/Digital converter to sample the signal from the receiver 18 at 100 MHz to 1 GHz. Cabling and connectors 20 are shown to connect the transducers 16 and 18 to the electronic devices. The digitized samples so triggered are transferred to a computer for the determination of the transmission time and the calculation of sound velocity using the equations described herein.

Figure 1B:
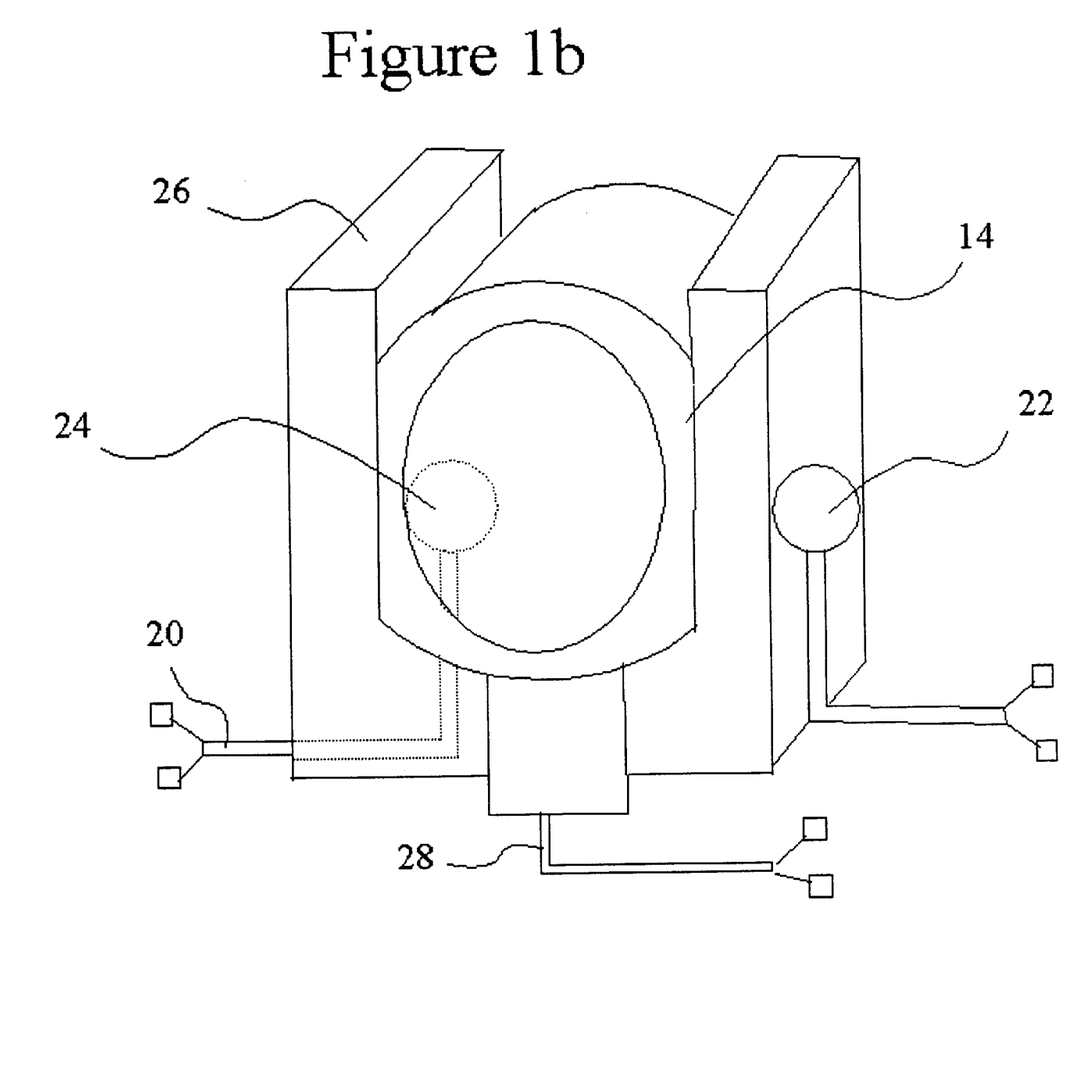
FIG. 1b is a schematic drawing of a second embodiment of the compressibility probe for which the transducers have no direct contact with the flowing blood.

In FIG. 1b, a second embodiment of the compressibility probe is described. In this embodiment, the probe exists in a clip 26, which is mounted with the ultrasound emitting transducer 22 and the receiving transducer 24. The surfaces of the transducers 22 and 24 are directly in contact with the tubing 14 inserted into the clip 26. The tubing 14 is connected to an extracorporeal circuit for fluid (blood, plasma or saline) to complete treatment. Cabling and connectors 20 transmit the power from a functional generator or a phase lock amplifier to activate the emitting transducer 22 into producing a continuous wave of ultrasound at a frequency in the range of about 10 to 30 Megahertz. The power signal is used as a reference signal by the phase lock amplifier. The receiving transducer 24 receives the ultrasound wave and sends it to the phase lock amplifier for the determination of its time shift from the reference signal. In this embodiment, the clip 26 has a gap about 5 mm for the insertion of the tubing 14 whose outside diameter is about 6.2 mm. Tubing with a diameter other than 6.2 mm can be used in the system and the dimensioning adjustments to the clip will be obvious to those skilled in the art. Ultrasound gel is used to facilitate the insertion of the tubing 14 into the clip and to provide an airtight contact between the tubing 14 and the transducers 22, 24, preventing errors that can be caused by the reflection of ultrasound through air bubbles. A sensor 28 measures the temperature of flowing blood. The temperature is used to correct the density assessment to the same temperature for the computation of the density change produced by a saline dilution protocol or as the patient responds to treatment. The entire clip-on compressibility probe is housed in an insulator to assure the temperature at the sensor 28 is identical to that of the flowing blood.

Figure 2:
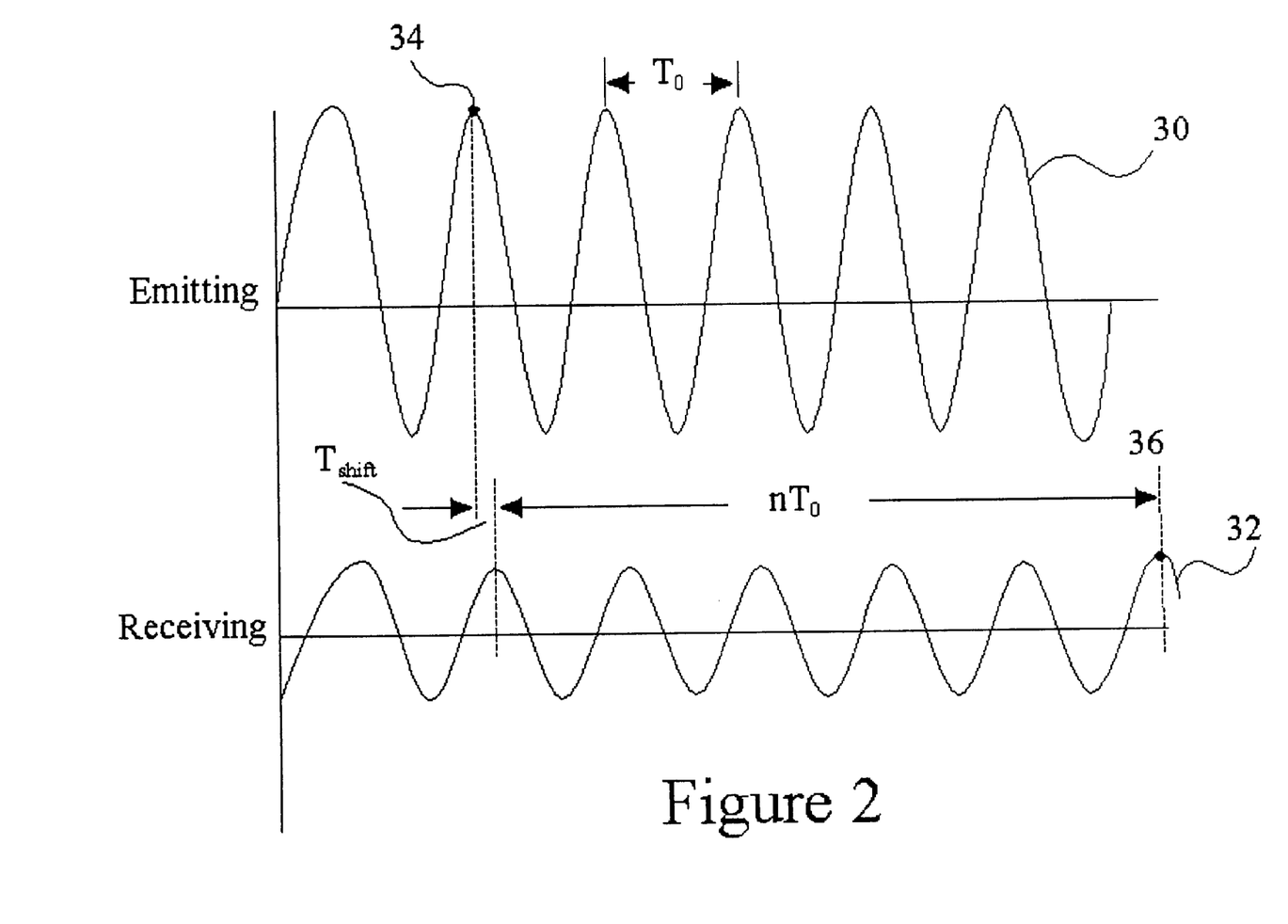
FIG. 2 is an illustration of the sound waves used to calculate the time shift, the overall transmission time, and subsequently the compressibility and density.

Using the clip-on compressibility probe, the processing of the transducer signals to assess the transmission time of ultrasound through blood is shown in FIG. 2. A reference signal is generated by the functional generator that is identical to the ultrasound wave 30 generated by the transducer of FIG. 1b. A second signal is transmitted by the receiving transducer 24 as it receives the ultrasound wave, which has been transmitted through the wall of the tube 14 and blood. The phase lock amplifier determines the time shift $T_{shift}$ through the mixing of the reference and received signals. For the purpose of illustration, the ultrasound peak 34 is transmitted to become the peak 36. The overall time delay on ultrasound transmission is the sum of the time shift and a multiple of ultrasound period ($nT_0$). After further correction on signal delay through cables and transducers, the transmission time is processed to determine the sound velocity and then compressibility or density through Equations 1, 2 and 3.

Figure 3:
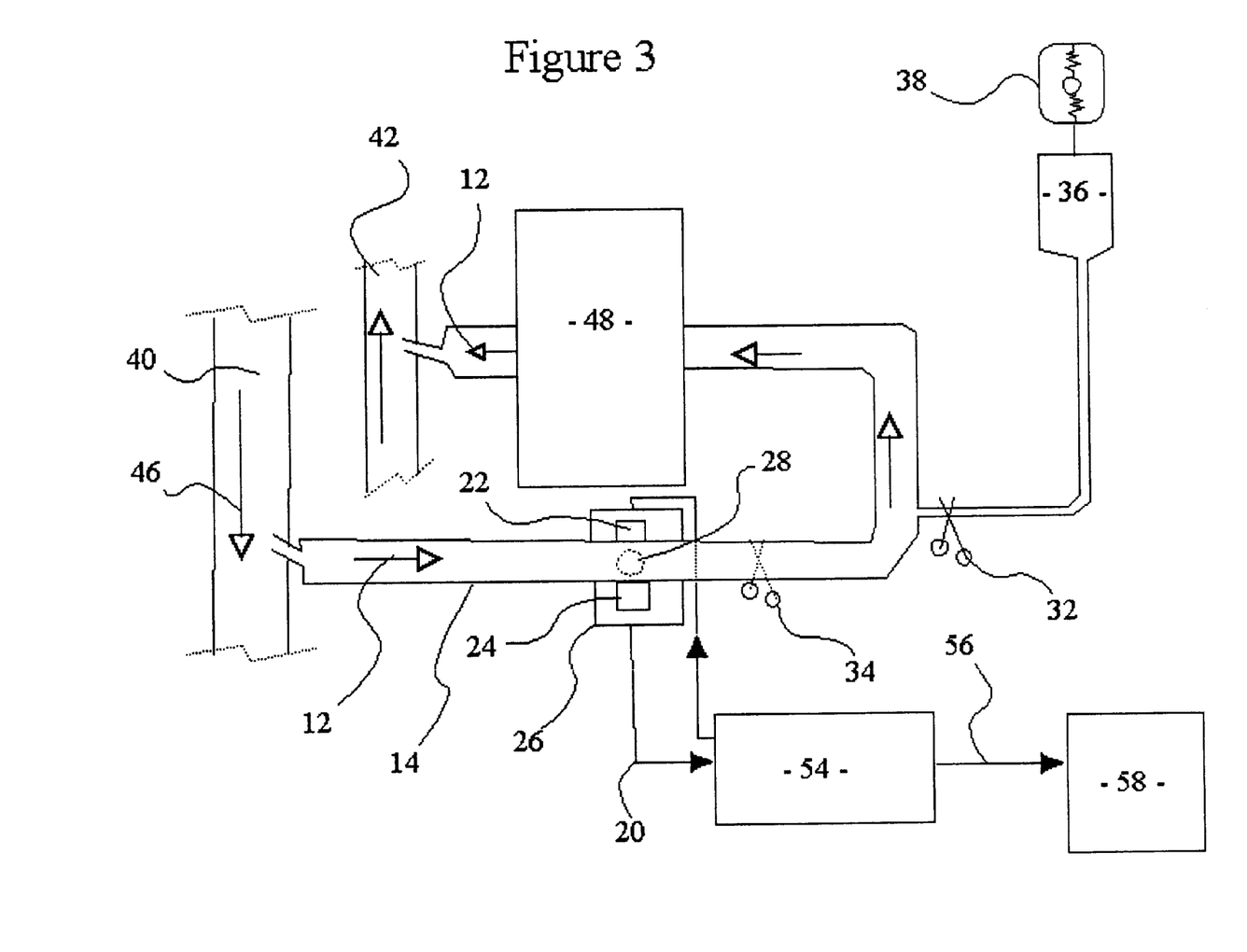
FIG. 3 is a schematic drawing of the compressibility probe as it is used to measure blood compressibility via blood flowing through the tubing of an extracorporeal system.

The integration of the clip-on compressibility probe with a dialysis system is shown schematically in FIG. 3. Tubing 14 leads from a blood vessel of a patient to an extracorporeal system 48 such as a dialysis system with a pump, a bubble trap and a hemodialysis filter. In the illustrated embodiment, the blood vessel is an artery 40 of a patient. A portion of the blood 46 flowing through the artery 40 is drawn into the tubing 14 for delivery through the clip-on compressibility probe 26 to the extracorporeal system 48. Between the compressibility probe 26 and the extracorporeal system 48, the tubing 14 is connected to a saline bag 36, which is mounted onto a weighing scale 38. Normally, a hemostat 32 clamps up the tubing connecting the saline bag to the tubing 14. For the infusion of saline into the circulation, the hemostat 32 is released and repositioned by clamping the hemostat 34 on the tubing 14 as shown to stop the blood flow coming from vessel 40. A pump in the extracorporeal system 48 withdraws the saline from the saline bag 36. When a preset volume of saline is infused as recognized by the weighing scale 38, the repositioned hemostat 34 is released and returned to its original position 32. The saline infusion is completed within about one-half minute. The blood 12 eventually is returned to the patient's circulation through the connection to a blood vessel, such as the illustrated vein 42. The transducers 22 and 24 in the clip-on probe 26 respectively emits and receives the ultrasound waves which are passed via cabling 20 to the phase lock amplifier 54 for the processing of the ultrasound signals. The processed information is relayed via cabling 56 to the evaluating device 58 where overall transmission time, sound velocity, compressibility and density over the state before and 2–5 minutes after the saline is infused are calculated. The signal from the temperature sensor 28 is also transmitted along this path, through cable 20, to the phase lock amplifier 54 and then to the evaluating device 58. Alternatively, the temperature can be transmitted directly from the temperature sensor 28 to the evaluating device 58. The transmission path of the temperature is dependent upon the final calculations and will be evident to those skilled in the art. Temperature is incorporated in the calculations using the equations described herein.

Figure 4A:
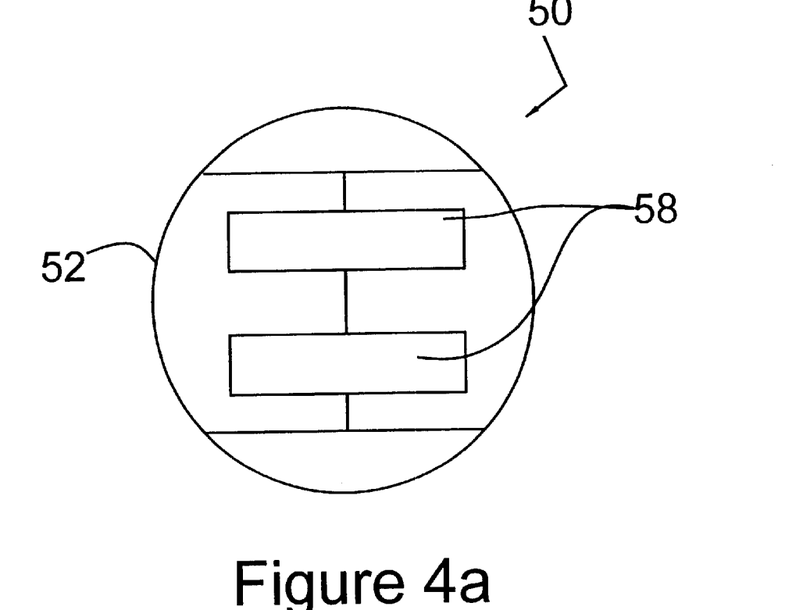
FIG. 4a is a top view of one embodiment of the tip of an intravascular probe.
Figure 4B:
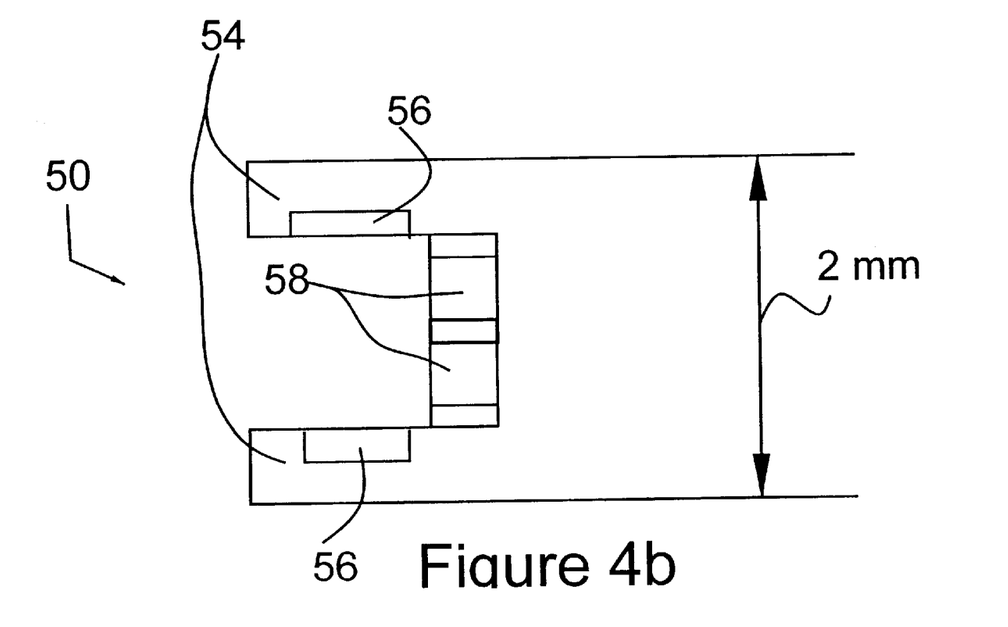
FIG. 4b is a side view of one embodiment of the tip of an intravascular probe.

FIGS. 4a and 4b show a detailed view of the tip of an additional embodiment of an intravascular probe 50 for determining blood compressibility and density. In FIG. 4a, the tip 52 of the intravascular probe 50 is seen in a bottom facing view. The tip 52 of the intravascular probe 50 takes a generally circular configuration for ease of placement into the blood vessel. In the embodiment illustrated herein the diameter is about 2 mm but this can be adjusted for use in different sized blood vessels or for use in animals. Blood flows between the two arms 54 of the forked probe to the ultrasound transducer and receiver 56 which are mounted on the inside surfaces of the fork arms 54. The probe arms 54 can be of a flat or beveled configuration. Two or more fiber bundles 58 are mounted on surface between the arms 54 and are used to assess the optical properties of the blood as it passes by the tip 52. This configuration permits the characterization of, for example, hematocrit and oxygen saturation of the blood, simultaneous with the ultrasound evaluation of density and compressibility. The fiber bundles 58 are constructed to form the shape of a two dimensional cone thereby enabling blood to flow between the fork arms 54 and over the cones 58. Transmission time of the ultrasound signal is measured as described to determine compressibility of the blood and the information is relayed to the evaluating device to determine density. To determine hematocrit and oxygen saturation, one fiber bundle transmits light to the blood and the other receives the reflected light.

A side view of the intravascular probe tip 50 is seen in FIG. 4b. The ultrasound transducer and receiver 56 are mounted on the inside surfaces of the fork arms 54. Two or more fiber bundles 58 are mounted on surface between the arms 54 and are used to assess the optical properties of the blood as it passes by the tip. In this view the fork arms are shown with a flat appearance; these may be beveled as well.

Additional embodiments of the clip-on compressibility and intravascular probes will become apparent to those of ordinary skill in the art.

What is claimed is:

1. A process for monitoring changes in blood volume and microvascular pooling in animals, comprising:

an extracorporeal blood treatment device in which blood from said blood system is conducted through a first branch of said extracorporeal system which is connected by tubing to an arterial segment of said blood system into a dialyzer or filter and returned via a second branch of said extracorporeal system said second branch connected by tubing to a venous segment of said blood system;

a diagnostic apparatus attached to said blood system for transmission and detection of ultrasound through blood flowing in the extracorporeal system;

a signal processing system to determine the time shift between the emitting and receiving ultrasound for determination of blood parameters;

an injection connection for infusing accurately a known amount of an indicator fluid to said blood system downstream of said diagnostic apparatus;

an indicator fluid infusion process to change the density of said blood system as measured through said diagnostic apparatus;

a control unit linked to said diagnostic apparatus for detecting compressibility with high resolution, for assessing density change at the same temperature, for initiating and recording ultrasound waves, and for monitoring the characteristics of said modified blood; and a computer memory unit for determining blood volume and microvascular pooling from said compressibility and density change.

2. The process of claim 1 wherein said animal is a human.

3. The process of claim 1 wherein said diagnostic apparatus is a clip-on ultrasound transducer and an ultrasound receiver mounted to a base.

4. The process of claim 3 wherein a temperature sensor is added to said diagnostic apparatus.

5. The process of claim 3 wherein said diagnostic apparatus is clipped onto the tubing of said extracorporeal blood treatment system.

6. The process of claim 1 wherein said indicator fluid is isotonic saline or dialysate.

7. The process of claim 1 wherein a dilution protocol is added wherein a known volume of said saline or dialysate is infused into said blood system.

8. The process of claim 5 wherein said ultrasound transducers are tightly clipped onto said tubing of said extracorporeal system for transmission of ultrasound.

9. The process of claim 1 wherein said ultrasound signals are processed by a phase lock amplifier to determine a time shift between emitting and receiving ultrasound.

10. The process of claim 9 wherein a calibration protocol employing two fluids of known sound velocity is used to determine the overall transmission time and the sound velocity for compressibility and density assessment of blood from said time shift.

11. A method for monitoring a patient's blood flow through use of a compressibility probe.

12. The method of claim 11 wherein said monitoring is calculating blood volume from density changes in blood flowing through an extracorporeal system as monitored by a compressibility probe.

13. The method of claim 12 where repeated dilutions are introduced to assess blood volume changes on hourly basis over the course of treatment.

14. The method of claim 11 wherein said monitoring is calculating microvascular pooling from density changes produced by volume shifts to a patient's microcirculation as monitored by a compressibility probe.

15. A process for monitoring changes in blood volume and microvascular pooling in animals, comprising:

a diagnostic apparatus attached to said blood system for transmission and detection of ultrasound through blood flowing in the extracorporeal system;

a signal processing system to determine the time shift between the emitting and receiving ultrasound for determination of blood parameters;

a control unit linked to said diagnostic apparatus for detecting compressibility with high resolution, for assessing density change at the same temperature, for initiating and recording ultrasound waves, and for monitoring the characteristics of said modified blood; and a computer memory unit for determining blood volume and microvascular pooling from said compressibility and density change.

16. The process of claim 15 wherein said animal is a human.

17. The process of claim 15 wherein said diagnostic apparatus is a clip-on ultrasound transducer and an ultrasound receiver mounted to a base.

18. The process of claim 17 wherein a temperature sensor is added to said diagnostic apparatus.

19. The process of claim 17 wherein said diagnostic apparatus is clipped onto an artery or a vein of said blood system.

20. An apparatus for monitoring changes in blood volume and microvascular pooling in animals, comprising:

an extracorporeal blood treatment device having a first branch, said first branch having a first end and a second end, said first end being connected by tubing to an arterial segment of the animal's blood system and said second end being connected to a filtration member; and a second branch, said second branch having a first end and a second end, said first end being connected by tubing to a venous segment of the animal's blood system and said second end being connected to said filtration member;

a diagnostic apparatus attached to said animal's blood system for transmission and detection of ultrasound through blood flowing in said extracorporeal device;

a signal processing system to determine the time shift between the emitting and receiving ultrasound for determination of blood parameters;

an injection connection for infusing accurately a known amount of an indicator fluid to said animal's blood system downstream of said diagnostic apparatus;

an indicator fluid infusion process to change the density of the animal's blood system as measured through said diagnostic apparatus;

a control unit linked to said diagnostic apparatus for detecting compressibility with high resolution, for assessing density change at the same temperature, for initiating and recording ultrasound waves, and for monitoring the characteristics of said modified blood; and a computer memory unit for determining blood volume and microvascular pooling from said compressibility and density change.

21. The device of claim 20 wherein said diagnostic device has a U-shaped probe, each leg of said probe having an ultrasound transducer positioned to oppose one another and a base of said U-shaped probe having at least a pair of fiber bundles, one of said pair transmitting light and a second of said pair receiving light reflection, wherein said ultrasound transducers measure compressibility and density of blood and said pair of fiber bundles measure hematocrit and oxygen saturation of said blood.

* * * * *